United States Patent
Lange et al.

(10) Patent No.: US 11,103,440 B2
(45) Date of Patent: Aug. 31, 2021

(54) AGENT AND METHOD FOR THE TEMPORARY DEFORMATION OF KERATIN-CONTAINING FIBERS

(71) Applicant: Henkel AG & Co. KGaA, Duesseldorf (DE)

(72) Inventors: Julia Bibiane Lange, Bad Bramstedt (DE); Diane Metten, Hamburg (DE); Cyrielle Martinez, Hamburg (DE)

(73) Assignee: HENKEL IP & HOLDING GMBH, Duesseldorf (DE)

( * ) Notice: Subject to any disclaimer, the term of this patent is extended or adjusted under 35 U.S.C. 154(b) by 0 days.

(21) Appl. No.: 16/140,960

(22) Filed: Sep. 25, 2018

(65) Prior Publication Data

US 2019/0099358 A1   Apr. 4, 2019

(30) Foreign Application Priority Data

Sep. 29, 2017   (DE) ..................... 10 2017 217 455.2

(51) Int. Cl.
*A61K 8/81*       (2006.01)
*A61Q 5/06*       (2006.01)

(52) U.S. Cl.
CPC .......... *A61K 8/8152* (2013.01); *A61K 8/8176* (2013.01); *A61K 8/8182* (2013.01); *A61Q 5/06* (2013.01); *A61K 2800/594* (2013.01)

(58) Field of Classification Search
None
See application file for complete search history.

(56) References Cited

U.S. PATENT DOCUMENTS

| | | | | |
|---|---|---|---|---|
| 5,021,238 A | * | 6/1991 | Martino | ................. A61K 8/046 424/47 |
| 2011/0135589 A1 | | 6/2011 | Knappe et al. | |
| 2014/0348770 A1 | | 11/2014 | Mueller et al. | |

FOREIGN PATENT DOCUMENTS

| | | | | |
|---|---|---|---|---|
| EP | 1671674 A1 | | 6/2006 | |
| EP | 3069709 A1 | * | 9/2016 | ............... A61Q 5/06 |
| EP | 3069709 A1 | | 9/2016 | |
| WO | 2011044306 A1 | | 4/2011 | |
| WO | 2013072162 A2 | | 5/2013 | |
| WO | 2013091993 A2 | | 6/2013 | |
| WO | 2017156756 A1 | | 9/2017 | |

* cited by examiner

*Primary Examiner* — Melissa S Mercier
(74) *Attorney, Agent, or Firm* — Lorenz & Kopf, LLP

(57) ABSTRACT

A cosmetic composition for temporarily reshaping keratin fibres, said composition containing:
a) at least one non-cross-linked, hydrophobically modified (meth)acrylic acid copolymer
b) at least one vinyl caprolactam copolymer,
use thereof, and method utilising a composition of this kind.

9 Claims, No Drawings

AGENT AND METHOD FOR THE TEMPORARY DEFORMATION OF KERATIN-CONTAINING FIBERS

CROSS-REFERENCE TO RELATED APPLICATION

This application claims priority to German Patent Application No. 10 2017 217 455.2, filed Sep. 29, 2017, which is incorporated herein by reference in its entirety.

TECHNICAL FIELD

The present disclosure relates to a cosmetic composition based on two specific copolymers for firming hair or for temporarily reshaping keratin fibres, in particular human hair, and a method and utilisation of this composition, and use thereof to improve long-term hold and resistance to moisture.

BACKGROUND

The temporary shaping of hairstyles for a relatively long period of time up to several days generally requires the application of firming active ingredients. Hair treatment agents that serve to temporarily shape the hair thus play an important role. Appropriate agents for temporary deformation usually contain synthetic polymers and/or wax as firming active ingredient. Agents for assisting the temporary reshaping of keratinous fibres can be provided for example in the form of hairspray, hair wax, hair gel or hair mousse.

The most important property of an agent for the temporary deformation of hair, also referred to hereinafter as styling agents, lies in providing the treated fibres with the greatest possible hold in the newly modelled form—i.e. a form impressed on the hair. Reference is also made to a strong hairstyle hold or to a high holding power of the styling agent. The hold of a hairstyle is determined fundamentally by the type and quantity of the used firming active ingredient, however the further constituents of the styling agent can also have an effect.

In addition to a high holding power, styling agents must also satisfy a wide range of further requirements. These can be divided roughly into properties on the hair, properties of the particular formulation, for example properties of the mousse, of the gel, or of the sprayed aerosol, and properties that concern the handling of the styling agent, wherein the properties on the hair are attributed particular importance. In particular, moisture resistance, low stickiness (tack), and a balanced conditioning effect can be cited. Furthermore, a styling agent should be universally usable for all hair types where possible and should be mild on the hair and skin.

In order to satisfy the different requirements, a multiplicity of synthetic polymers which are used in styling agents have already been developed as firming active ingredients. These polymers can be divided into cationic, anionic, nonionic and amphoteric firming polymers.

European patent application EP 3 069 709 A1 describes cosmetic polymer blends for the hair which, besides an oxyalkylene polymer, also contain the hydrophobically modified (meth)acrylic acid copolymer with the commercial name Luvigel Fit (International Nomenclature Cosmetic Ingredient (INCI): Acrylates (C10-30) Alkyl Methacrylate Copolymer)

International patent application WO 2013/091993 A1 describes a styling agent based on a specific polymer combination comprising a polymer with the INCI name Vinyl Caprolactam/VP/Dimethylaminoethyl Methacrylate Copolymer.

When applied to the hair, the polymers ideally form a polymer film on the hair that on the one hand provides the hairstyle with a strong hold, but on the other hand is sufficiently flexible so as not to break when stressed. If the polymer film is too brittle, what are known as film flakes form, that is to say residues that detach as the hair moves and give the impression that the user of the corresponding styling agent has dandruff. Similar problems are encountered when wax is used as firming active ingredient in the styling agent. If the styling agent is a gel or a paste, the polymers should additionally have thickening properties.

BRIEF SUMMARY

Cosmetic compositions for temporarily reshaping keratin fibres and methods for the temporary deformation of keratinous fibres are provided herein. In an embodiment, a cosmetic composition for temporarily reshaping keratin fibres includes a) at least one non-cross-linked, hydrophobically modified (meth)acrylic acid copolymer and b) at least one vinyl caprolactam copolymer.

In another embodiment, a cosmetic composition for the temporary shaping of keratinic fibers includes a) at least one non-cross-linked, hydrophobically modified (meth)acrylic acid copolymer, b) at least one vinyl caprolactam copolymer, c) polyvinylpyrrolidone, and water. The a) at least one non-cross-linked, hydrophobically modified (meth)acrylic acid copolymer is selected from the group of compounds with the INCI name Acrylates/$C_{10-30}$ Alkyl Methacrylate Copolymer and is present in an amount of from about 0.5 to about 7.0% by weight. The b) at least one vinyl caprolactam copolymer is selected from the group of compounds with the INCI name Vinyl Caprolactam/VP/Dimethylaminoethyl Methacrylate Copolymer and/or compounds with the INCI name VP/Vinyl Caprolactam/DMAPA Acrylates Copolymer, and is present in an amount of from about 0.1 to about 5.0% by weight. The c) polyvinylpyrrolidone is present in an amount of from about 3.0 to about 7.0% by weight. The water is present in an amount of at least 70% by weight. All amounts are based on the total weight of the cosmetic composition.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

One object of the present disclosure was to provide a further suitable polymer combination which is exemplified by good film-forming and/or firming properties, a very high degree of hold without having to compromise on flexibility and good moisture resistance—in particular resistance to perspiration and water—and which additionally is suitable for the production of stable viscous and stable transparent cosmetic compositions. In particular, currently available styling agents can be improved even further in that a good combination of stiffness and long-term hold (high humidity curl retention) is not always ensured sufficiently. One object of the present disclosure is therefore to provide styling agents that, besides the above-mentioned properties, in particular also produce good stiffness and a good long-term hold.

This has been achieved as contemplated herein by a combination of two specific anionic copolymers.

The following is provided by employing the present disclosure:

A cosmetic composition for the temporary reshaping of keratin fibres, containing:
a) at least one non-cross-linked, hydrophobically modified (meth)acrylic acid copolymer
b) at least one vinyl caprolactam copolymer.

The cosmetic composition as contemplated herein, wherein the proportion by weight of the copolymer a) in the total weight of the composition is from about 0.1 to about 15% by weight, preferably from about 0.2 to about 10% by weight, and in particular from about 0.5 to about 7.0% by weight.

The cosmetic composition as contemplated herein, wherein the copolymer a) is obtained by reacting
at least one monomer (a1) from the group of acrylic acid, methacrylic acid, $C_1$-$C_6$ alkyl acrylic acid ester, $C_1$-$C_6$ alkyl methacrylic acid ester, with
at least one monomer (a2) from the group of $C_{10-30}$ alkyl acrylate, $C_{10-30}$ alkyl methacrylate, $C_{10-30}$ alkyl PEG acrylate, $C_{10-30}$ alkyl PEG methacrylate or $C_{10-30}$ alkyl PEG itaconate.

The cosmetic composition as contemplated herein, wherein the copolymer a) is obtained by reacting
at least one monomer (a1) from the group acrylic acid, methacrylic acid with
at least one monomer (a2) from the group of $C_{10-30}$ alkyl methacrylate.

The cosmetic composition as contemplated herein, wherein the copolymer a) is selected from the group of compounds with the INCI name Acrylates/$C_{10-30}$ Alkyl Methacrylate Copolymer.

The cosmetic composition as contemplated herein, wherein the proportion by weight of the copolymer b) in the total weight of the composition is from about 0.05 to about 10% by weight, preferably from about 0.05 to about 7.0% by weight, and in particular from about 0.1 to about 5.0% by weight.

The cosmetic composition as contemplated herein, wherein the copolymer b) is obtained by reacting N-vinyl caprolactam with N-vinylpyrrolidone and N,N-dimethylaminoethyl methacrylate.

The cosmetic composition as contemplated herein, wherein a terpolymer of N-vinyl caprolactam, N-vinylpyrrolidone and N,N-dimethylaminoethyl methacrylate is used as copolymer b).

The cosmetic composition as contemplated herein, wherein the copolymer b) is selected from the group of compounds with the INCI name Vinyl Caprolactam/VP/Dimethylaminoethyl Methacrylate Copolymer.

The cosmetic composition as contemplated herein, wherein the copolymer b) is obtained by reacting N-vinyl caprolactam with N-vinylpyrrolidone and N,N-dimethylaminopropyl methacrylamide.

The cosmetic composition as contemplated herein, wherein a terpolymer of N-vinyl caprolactam, N-vinylpyrrolidone and N,N-dimethylaminopropyl methacrylamide is used as copolymer b).

The cosmetic composition as contemplated herein, wherein the copolymer b) is selected from the group of compounds with the INCI name VP/Vinyl Caprolactam/DMAPA Acrylates Copolymer.

The cosmetic composition as contemplated herein, wherein the ratio by weight of copolymer a) to copolymer b) is from about 10:1 to about 1:10, preferably from about 5:1 to about 1:5 and in particular from about 3:1 to about 1:3.

The cosmetic composition as contemplated herein, exemplified in that it also contains
c) polyvinylpyrrolidone and/or vinylpyrrolidone/vinyl acetate copolymer, preferably polyvinylpyrrolidone.

The cosmetic composition as contemplated herein, wherein the proportion by weight of the polyvinylpyrrolidone and/or vinylpyrrolidone/vinyl acetate copolymer c) in the total weight of the cosmetic composition is from about 0.1 to about 10% by weight, preferably from about 2.0 to about 8.5% by weight, and in particular from about 3.0 to about 7.0% by weight.

The cosmetic composition as contemplated herein, wherein the composition, based on its total weight, contains from about 0.05 to about 2.0% by weight, preferably from about 0.1 to about 1.0% by weight, and in particular from about 0.1 to about 0.5% by weight of an amino alcohol, preferably 2-amino-2-methylpropanol.

The cosmetic composition as contemplated herein, wherein the composition, based on its total weight, contains at least about 20% by weight, preferably at least about 40% by weight, and in particular at least about 70% by weight of water.

The cosmetic composition as contemplated herein, exemplified in that the agent is present in the form of hair gel, hairspray, hair mousse or hair wax.

Use of a cosmetic composition as contemplated herein for the temporary deformation of keratinous fibres, in particular human hair.

Use of a cosmetic composition as contemplated herein for improving the hold of temporarily deformed keratin fibres.

Use of a cosmetic composition as contemplated herein, for improving the moisture resistance of temporarily deformed keratin fibres.

A method for the temporary deformation of keratinous fibres, in particular human hair, in which the keratin fibres are exposed to a cosmetic composition as contemplated herein and are fixed temporarily in their form.

It has surprisingly been found within the scope of the present disclosure that an improved hold of styling products can be achieved by combining two constituents known per se which are already used in styling products. Other properties usually required of styling products, such as resistance to moisture, stiffness and low tack, are retained. A good combination of properties of this kind was not anticipated, not even in the knowledge of the individual components, and was surprising. It has been found by way of experimentation that an effect going significantly beyond a mere additive effect of said constituents, i.e. a synergistic effect, is obtained in respect of the hold and was demonstrated in the HHRC test (high humidity curl retention test).

The term "keratin fibres" as contemplated herein comprises fur, wool and feathers, but in particular human hair.

The key constituents of the cosmetic composition are the non-cross-linked, hydrophobically modified copolymer a) and the vinyl caprolactam copolymer b) different from the copolymer a).

Besides the above-mentioned advantages, the cosmetic compositions are exemplified compared to alternative cosmetic agents also by an improved long-term hold. A ratio by weight of the polymers a) and b) in the cosmetic composition of from about 10:1 to about 1:10, preferably from about 5:1 to about 1:5, and in particular from about 3:1 to about 1:3 has proven to be particularly advantageous for the cosmetic properties of the agents as contemplated herein, for example the resistance to moisture and low tack.

The cosmetic compositions, as first compulsory component, contain a non-cross-linked, hydrophobically modified (meth)acrylic acid copolymer which is constructed from at least two different structural units. In addition, further structural units can be provided.

Copolymers that can be traced back to
at least one monomer (a1) from the group of unsaturated carboxylic acids and unsaturated carboxylic acid esters, and
at least one monomer (a2) from the group of unsaturated hydrophobically modified monomers are preferably used as hydrophobically modified (meth)acrylic acid copolymers a).

Preferred copolymers a) are based on at least one monomer (a1) from the group acrylic acid, methacrylic acid, $C_1$-$C_6$ alkylacrylic acid ester, $C_1$-$C_6$ alkylmethacrylic acid ester. The acrylic acid esters and methacrylic acid esters are preferably esters of the respective acids with non-tertiary alkyl alcohols with alkyl groups of from about 1 to about 12 carbon atoms, in particular from about 2 to about 4 carbon atoms. Examples of suitable monomers are ethyl acrylate, ethyl methacrylate, propyl acrylate, propyl methacrylate, n-butyl acrylate, n-butyl methacrylate, isobutyl acrylate, 2-methylbutyl acrylate, 2-ethylhexyl acrylate, n-octyl acrylate, isooctyl acrylate, isooctyl methacrylate, isononyl acrylate and isodecyl acrylate.

The group of hydrophobically modified monomers (a2) denotes monomers that have a hydrophobic sub-structure. Preferred monomers (a2) can be traced back in turn to the two following structural units:
an unsaturated acid, preferably acrylic acid, methacrylic acid or itaconic acid; a $C_{8-40}$ alkyl chain, preferably a $C_{10-30}$ alkyl chain,
These two sub-structures can be supplemented optionally by a third structural unit from the group of polyoxyalkylene groups, preferably the polyethylene glycol groups, the polypropylene glycol groups, or the polyethylene glycol/polypropylene glycol groups.

For example, $C_{10-30}$ alkyl acrylate, $C_{10-30}$ alkyl PEG acrylate, $C_{10-30}$ alkyl PEG methacrylate or $C_{10-30}$ alkyl PEG itaconate are used as monomer (a2). Preferred monomers (a2) are selected from the $C_{10-30}$ alkyl acrylates, $C_{10-30}$ alkyl PEG 20-25 acrylates, $C_{10-30}$ alkyl PEG 20-25 methacrylates or $C_{10-30}$ alkyl PEG 20-25 itaconates. Particularly preferred monomers (a2) are selected from the group of $C_{10-30}$ alkyl methacrylates.

Copolymers a) that are obtained by reacting
at least one monomer (a1) selected from the group acrylic acid, methacrylic acid, $C_1$-$C_6$ alkyl acrylic acid esters, and $C_1$-$C_6$ alkyl methacrylic acid esters with
at least one monomer (a2) from the group of $C_{10-30}$ alkyl acrylate, $C_{10-30}$ alkyl methacrylate, $C_{10-30}$ alkyl PEG acrylate, $C_{10-30}$ alkyl PEG methacrylate or $C_{10-30}$ alkyl PEG itaconate are particularly preferred.

Copolymers a) obtained by reacting
at least one monomer (a1) from the group acrylic acid, methacrylic acid with
at least one monomer (a2) from the group of $C_{10-30}$ alkyl methacrylate are very particularly preferred.

To summarise, cosmetic agents that are preferred as contemplated herein are exemplified in that the copolymer a) is selected from the group of compounds with the INCI names Acrylates/$C_{10-30}$-Alkyl Methacrylate Copolymer, Acrylates/Steareth-20 Methacrylate Copolymer, Acrylates/Beheneth-25 Methacrylate Copolymer, Acrylates/Steareth-20 Itaconate Copolymer, Acrylates/Ceteth-20 Itaconate Copolymer, Acrylates/Palmeth-25 Acrylate Copolymer, Acrylates/Aminoacrylates/$C_{10-30}$ Alkyl PEG-20 Itaconate Copolymer. Corresponding polymers are obtainable for example under the commercial names Luvigel® FIT, Aculyn® 22, Aculyn® 28, Structure® 2001, Structure® 3001, Synthalen® W2000 and Structure® Plus. The copolymer a) is particularly preferably selected from the group of compounds with the INCI name Acrylates/$C_{10-30}$ Alkyl Methacrylate Copolymer.

The proportion by weight of the copolymer a) in the total weight of the composition is preferably from about 0.1 to about 15% by weight, particularly preferably from about 0.2 to about 10% by weight, and in particular from about 0.5 to about 7.0% by weight.

The copolymer a) is preferably used in partially neutralised or neutralised form in the cosmetic composition. At least one alkanolamine is preferably used for the neutralisation. The alkanolamines that can be used as alkalising agent as contemplated herein are preferably selected from primary amines having a $C_2$-$C_6$ alkyl parent substance carrying at least one hydroxyl group. Particularly preferred alkanolamines are selected from the group formed from 2-aminoethan-1-ol (monoethanolamine), tris(2-hydroxyethyl)-amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. Alkanolamines that are very particularly preferred as contemplated herein are selected from the group of 2-aminoethan-1-ol, 2-amino-2-methylpropan-1-ol and 2-amino-2-methyl-propan-1,3-diol. A particularly suitable neutralising agent here has proven to be 2-amino-2-methylpropanol. Cosmetic compositions that are preferred as contemplated herein contain at least one alkanolamine, preferably 2-amino-2-methylpropanol. 2-amino-2-methylpropanol is used in the composition as contemplated herein preferably in a quantity that does not exceed the quantity required for neutralisation of the copolymer a). The quantities of 2-amino-2-methylpropanol used in the compositions as contemplated herein is preferably from about 80 to about 100%, particularly preferably from about 90 to about 100%, and in particular from about 95 to about 100% of the quantity required for full neutralisation of the copolymer a). Proportions by weight of the amino alcohol, preferably of the 2-amino-2-methylpropanol, in the total weight of the cosmetic composition are very particularly preferably from about 0.05 to about 2.0% by weight, preferably from about 0.1 to about 1.0% by weight, and in particular from about 0.1 to about 0.5% by weight.

A second essential constituent of the cosmetic composition is the vinyl caprolactam copolymer b).

The copolymers b) used in the cosmetic compositions are preferably non-ionic or cationic.

Cationic polymers are understood to be polymers having a group that can be "temporarily" cationic or "permanently" cationic in the main and/or side chain.

As contemplated herein, "permanently cationic" polymers are those which comprise a cationic group irrespective of the pH value of the agent. These are generally polymers which contain a quaternary nitrogen atom, for example in the form of an ammonium group. Preferred cationic polymers are quaternary ammonium groups. Polymers in which the quaternary ammonium group is bonded via a C1-4 hydrocarbon group to a polymer main chain constructed from acrylic acid, methacrylic acid or derivatives thereof have proven to be particularly suitable.

"Temporarily cationic" polymers are those for which cationisation is dependent on the pH value. These polymers usually contain an amino group that is present in protic solvents as protonated ammonium group and is thus present in cationic form.

The copolymers b) are particularly preferably non-ionic or temporarily cationic.

Preferred cosmetic compositions contain a copolymer b) comprising at least one structural unit of formula (M1) and at least one structural unit of formula (M2) and at least one structural unit of formula (M3),

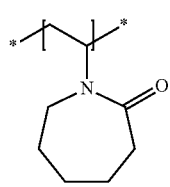
(M1)

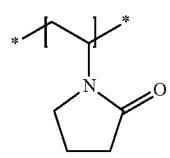
(M2)

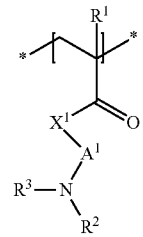
(M3)

in which
$R^1$ stands for a hydrogen atom or a methyl group,
$X^1$ stands for an oxygen atom or an NH group,
$A^1$ stands for an ethan-1,2-diyl, propan-1,3-diyl or butan-1,4-diyl group,
$R^2$ and $R^3$ stand independently of one another for a ($C_1$ to $C_4$) alkyl group.

$R^1$ in formula (M3) preferably stands for a methyl group.

Examples of ($C_1$ to $C_4$) alkyl groups according to formula (M3) are methyl, ethyl, isopropyl, n-propyl, n-butyl, sec-butyl, isobutyl and tert-butyl. $R^2$ and $R^3$ in formula (M3) preferably stand for a methyl group.

Very particularly suitable polymers of this embodiment comprise at least one structural unit of formula (M3), in which $A^1$ stands for an ethan-1,2-diyl group and $X^1$ stands for an oxygen atom.

Again, a polymer of this kind preferably comprises at least one structural unit of formula (M1) and at least one structural unit of formula (M2) and at least one structural unit of formula (M3-1)

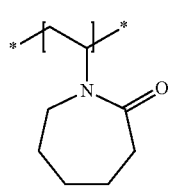
(M1)

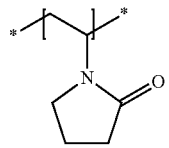
(M2)

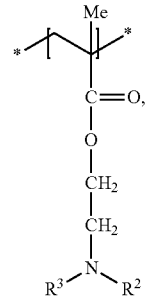
(M3-1)

in which $R^2$ and $R^3$ independently of one another stand for a ($C_1$ to $C_4$) alkyl group, in particular for methyl. Examples of ($C_1$ to $C_4$) alkyl groups according to formula (M3-1) are methyl, ethyl, isopropyl, n-propyl, n-butyl, sec-butyl, isobutyl and tert-butyl.

The cosmetic composition, as copolymer b), very particularly preferably contains a terpolymer of N-vinyl caprolactam, N-vinylpyrrolidone and N,N-dimethylaminoethyl methacrylate. Such copolymers can be obtained for example under the trade names Advantage LC-E (INCI name: Vinylcaprolactam/VP/Dimethylaminoethylmethacrylate Copolymer, Laurylpyrrolidone; about 37% by weight active substance in ethanol with addition of N-Laurylpyrrolidone), Advantage S (INCI name: Vinylcaprolactam/VP/Dimethylaminoethylmethacrylate Copolymer, 100% by weight active substance, powder) or Advantage LC-A (INCI name: Vinylcaprolactam/VP/Dimethylaminoethylmethacrylate Copolymer; about 37% by weight active substance in ethanol) from the company Ashland.

In a second preferred embodiment the copolymer b) is obtained by copolymerisation of the monomers N-vinylpyrrolidone, N-vinyl caprolactam and N,N-dimethylaminopropyl methacrylamide.

Preferred copolymers b) include to an extent at least about 90% by weight, preferably at least about 95% by weight, and in particular at least about 97% by weight of the monomers N-vinylpyrrolidone, N-vinyl caprolactam and N,N-dimethylaminopropyl methacrylamide. Particularly preferred copolymers b) are obtained exclusively from the monomers N-vinylpyrrolidone, N-vinyl caprolactam and N,N-dimethylaminopropyl methacrylamide. Such copolymers are obtainable for example under the trade name Aquaflex SF 40 (INCI name: VP/Vinyl Caprolactam/DMAPA Acrylates Copolymer, Alcohol Denat.; from about 38 to about 42% by weight active substance in ethanol) from the company ISP.

The proportion by weight of the copolymer b) in the total weight of the composition is preferably from about 0.05 to about 10% by weight, particularly preferably from about 0.05 to about 7.0% by weight, and in particular from about 0.1 to about 5.0% by weight.

The cosmetic composition of the present disclosure preferably contains one or more further polymers which is/are different from the copolymers a) and b) and for example assists/assist the thickening agents or the gel formation or the film formation. Examples are cationic, anionic, non-ionic or amphoteric polymers.

Examples are Acrylamide/Ammonium Acrylate Copolymer, Acrylamides/DMAPA Acrylates/Methoxy PEG Methacrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/t-Butylacrylamide Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/Octylacrylamide Copolymer, Acrylates/Octylacrylamide/Diphenyl Amodimethicone Copolymer, Acrylates/Stearyl Acrylate/Ethylamine Oxide Methacrylate Copolymer, Acrylates/VA Copolymer, Acrylates/VP Copolymer, Adipic Acid/Diethylenetriamine Copolymer, Adipic Acid/Dimethylaminohydroxypropyl Diethylenetriamine Copolymer, Adipic Acid/Epoxypropyl Diethylenetriamine Copolymer, Adipic Acid/Isophthalic Acid/Neopentyl Glycol/Trimethylolpropane Copolymer, Allyl Stearate/VA Copolymer, Aminoethylacrylate Phosphate/Acrylates Copolymer, Aminoethylpropanediol-Acrylates/Acrylamide Copolymer, Aminoethylpropanediol-AMPD-Acrylates/Diacetoneacrylamide Copolymer, Ammonium VA/Acrylates Copolymer, AMPD-Acrylates/Diacetoneacrylamide Copolymer, AMP-Acrylates/Allyl Methacrylate Copolymer, AMP-Acrylates/C1-18 Alkyl Acrylates/C1-8 Alkyl Acrylamide Copolymer, AMP-Acrylates/Diacetoneacrylamide Copolymer, AMP-Acrylates/Dimethylaminoethylmethacrylate Copolymer, Bacillus/Rice Bran Extract/Soybean Extract Ferment Filtrate, Bis-Butyloxyamodimethicone/PEG-60 Copolymer, Butyl Acrylate/Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide/Sodium Acrylate Copolymer, Diethylene Glycolamine/Epichlorohydrin/Piperazine Copolymer, Dimethicone Crosspolymer, Diphenyl Amodimethicone, Ethyl Ester of PVM/MA Copolymer, Hydrolyzed Wheat Protein/PVP Crosspolymer, Isobutylene/Ethylmaleimide/Hydroxyethylmaleimide Copolymer, Isobutylene/MA Copolymer, Isobutylmethacrylate/Bis-Hydroxypropyl Dimethicone Acrylate Copolymer, Isopropyl Ester of PVM/MA Copolymer, Lauryl Acrylate Crosspolymer, Lauryl Methacrylate/Glycol Dimethacrylate Crosspolymer, MEA-Sulfite, Methacrylic Acid/Sodium Acrylamidomethyl Propane Sulfonate Copolymer, Methacryloyl Ethyl Betaine/Acrylates Copolymer, Octylacrylamide/Acrylates/Butylaminoethyl Methacrylate Copolymer, PEG/PPG-25/25 Dimethicone/Acrylates Copolymer, PEG-8/SMDI Copolymer, Polyacrylamide, Polyacrylate-6, Polybeta-Alanine/Glutaric Acid Crosspolymer, Polybutylene Terephthalate, Polyester-1, Polyethylacrylate, Polyethylene Terephthalate, Polymethacryloyl Ethyl Betaine, Polypentaerythrityl Terephthalate, Polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polyquaternium-68, Polysilicone-9, Polyurethane-1, Polyurethane-6, Polyurethane-10, Polyvinyl Acetate, Polyvinyl Butyral, Polyvinylcaprolactam, Polyvinylformamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10 Ether, PPG-12/SMDI Copolymer, PPG-51/SMDI Copolymer, PPG-10 Sorbitol, PVM/MA Copolymer, PVP, PVP/VA/Itaconic Acid Copolymer, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia Urens Gum, Terephthalic Acid/Isophthalic Acid/Sodium Isophthalic Acid Sulfonate/Glycol Copolymer, Trimethylolpropane Triacrylate, Trimethylsiloxysilylcarbamoyl Pullulan, VA/Crotonates Copolymer, VA/Crotonates/Methacryloxybenzophenone-1 Copolymer, VA/Crotonates/Vinyl Neodecanoate Copolymer, VA/Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Dimethylaminoethyl Methacrylate Copolymer, VP/Acrylates/Lauryl Methacrylate Copolymer, VP/Dimethylaminoethylmethacrylate Copolymer, VP/DMAPA Acrylates Copolymer, VP/Hexadecene Copolymer, VP/VA Copolymer, VP/Vinyl Caprolactam/DMAPA Acrylates Copolymer, Yeast Palmitate and Styrene/VP Copolymer.

The further component acting as gel former is preferably a homopolyacrylic acid (INCI: Carbomer), which is commercially available under the name Carbopol® in various embodiments. The carbomer is preferably contained in a proportion of from about 0.02 to about 3% by weight, preferably from about 0.05 to about 1.5% by weight, and even more preferably from about 0.2 to about 0.8% by weight, in relation to the total weight of the cosmetic composition.

In order to further increase their cosmetic effect, besides the copolymers a) and b) and optionally added thickening agent or gel former, preferred compositions additionally contain a film-forming polymer c) different from these ingredients, in particular an anionic or non-ionic polymer c).

Examples of non-ionic polymers are:

Vinylpyrrolidone/vinyl ester copolymers, as are sold for example under the trademark Luviskol (BASF). Luviskol VA 64 and Luviskol VA 73, each vinylpyrrolidone/vinyl acetate copolymers, are preferred non-ionic polymers.

Cellulose ethers, such as hydroxypropyl cellulose, hydroxyethyl cellulose and methylhydroxypropyl cellulose, as are sold for example under the trade names Culminal and Benecel (AQUALON).

Shellac.

Polyvinylpyrrolidones, as are sold for example under the name Luviskol (BASF).

Siloxanes. These siloxanes can be both water-soluble and water-insoluble. Both volatile and non-volatile siloxanes are suitable, wherein compounds of which the boiling point at normal pressure is above about 200° C. are understood to be non-volatile siloxanes. Preferred siloxanes are polydialkylsiloxanes, such as polydimethyl siloxane, polyalkylaryl siloxanes, such as polyphenylmethyl siloxane, ethoxylated polydialkyl siloxanes, and polydialkyl siloxanes which contain amine and/or hydroxy groups.

Glycosidically substituted silicones.

On account of their cosmetic effect in combination with the copolymers a) and b), film-forming polymers used with preference as contemplated herein are in particular the polyvinylpyrrolidones (INCI name: PVP) and the vinylpyrrolidone/vinyl acetate copolymers (INCI name VP/VA copolymer). Primarily the holding properties, but also the application properties of the cosmetic compositions are advantageously influenced by the addition of film-forming polymers, in particular the aforementioned polyvinylpyrrolidones and vinylpyrrolidone/vinyl acetate copolymers. The proportion by weight of these polymers is preferably limited to amounts between about 1.0 and about 10% by weight. Preferred cosmetic compositions as contemplated herein are therefore exemplified in that they also contain, in relation to their total weight, between about 1.0 und about 10% by weight of polyvinylpyrrolidone and/or vinylpyrrolidone/vinyl acetate copolymer, preferably polyvinylpyrrolidone. Particularly preferred cosmetic agents have a proportion by weight of the polyvinylpyrrolidone and/or vinylpyrrolidone/vinyl acetate copolymer c) in the total weight of the cosmetic agent of from about 2.0 to about 8.5% by weight, preferably from about 3.0 to about 7.0% by weight.

The cosmetic composition as contemplated herein can contain further conventional substances of styling products. In particular, additional nourishing substances can be mentioned as further auxiliaries and additives.

As nourishing substances, the product can contain at least one protein hydrolysate and/or a derivative thereof, for example. Protein hydrolysates are product mixtures which are obtained by acid-catalysed, base-catalysed or enzymatically catalysed breakdown of proteins. The term "protein hydrolysates" is understood as contemplated herein to also mean total hydrolysates and also individual amino acids and derivatives thereof as well as mixtures of different amino acids. The molecular weight of the protein hydrolysates usable as contemplated herein lies between about 75, the molecular weight for glycine, and about 200,000, and the molecular weight is preferably from about 75 to about 50,000, and very particularly preferably from about 75 to about 20,000 daltons.

As nourishing substance, the agent as contemplated herein can also contain at least one vitamin, a provitamin, a vitamin precursor and/or one of the derivatives thereof. Here, vitamins, provitamins and vitamin precursors that are usually assigned to the groups A, B, C, E, F and H are preferred as contemplated herein.

Similarly to the addition of glycerol and/or propylene glycol, the addition of panthenol increases the flexibility of the polymer film formed with application of the product as contemplated herein.

As nourishing substance, the agents as contemplated herein can also contain at least one plant extract, but also monosaccharides or oligosaccharides and/or lipids.

Oil bodies are also suitable as nourishing substance. Natural and synthetic cosmetic oil bodies include, for example, plant oils, liquid paraffin oils, isoparaffin oils and synthetic hydrocarbons as well as di-n-alkyl ethers having a total of between about 12 and about 36 C atoms, in particular from about 12 to about 24 C atoms. Preferred cosmetic agents as contemplated herein contain at least one oil body, preferably at least one oil body from the group of silicone oils. The group of silicone oils includes, in particular, the dimethicones, which also include the cyclomethicones, the aminofunctional silicones, and also the dimethiconols. The dimethicones can be both linear and branched and cyclic, or cyclic and branched. Suitable silicone oils or silicone gums are in particular dialkyl and alkylaryl siloxanes, such as dimethyl polysiloxane and methylphenyl polysiloxane, and the alkoxylated, quaternised, or anionic derivatives thereof. Cyclic and linear polydialkyl siloxanes, the alkoxylated and/or aminised derivatives thereof, dihydroxypolydimethyl siloxanes and polyphenyl alkyl siloxanes are preferred.

Ester oils, i.e. esters of C6-C30 fatty acids with C2-C30 fatty alcohols, preferably monoesters of the fatty acids with alcohols having from about 2 to about 24 C atoms, such as isopropylmyristate (Rilanit® IPM), isononanoic acid C16-18 alkyl ester (Cetiol® SN), 2-ethylhexyl palmitate (Cegesoft® 24), stearic acid-2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanite® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), and oleic acid decyl ester (Cetiol® V) are further preferred nourishing oil bodies.

Furthermore, dicarboxylic acid esters, symmetrical, asymmetrical or cyclic esters of carbon dioxide with fatty alcohols, tri fatty acid esters of saturated and/or unsaturated linear and/or branched fatty acids with glycerol or fatty acid partial glycerides, which are understood to mean monoglycerides, diglycerides and technical mixtures thereof, are to be understood as nourishing substances.

Emulsifiers or surface-active agents are also preferably contained in the composition as contemplated herein. PEG derivatives of hydrogenated castor oil which are obtainable for example under the name PEG Hydrogenated Castor Oil are preferred, for example PEG-30 Hydrogenated Castor Oil, PEG-33 Hydrogenated Castor Oil, PEG-35 Hydrogenated Castor Oil, PEG-36 Hydrogenated Castor Oil, or PEG-40 Hydrogenated Castor Oil. The use of PEG-40 Hydrogenated Castor Oil is preferred as contemplated herein. These are preferably contained in an amount of from about 0.05 to about 1.5% by weight, more preferably from about 0.1 to about 1.0% by weight, also preferably from about 0.2 to about 0.8% by weight or from about 0.3 to about 0.6% by weight. Besides the tailored provision, in particular the ease with which the cosmetic compositions can be washed out is also improved by the addition of the surface-active substances, in particular the aforementioned PEG derivatives of hydrogenated castor oil.

The cosmetic compositions as contemplated herein contain the ingredients or active substances in a cosmetically acceptable carrier.

Preferred cosmetically acceptable carriers are aqueous, alcoholic, or aqueous-alcoholic media with preferably at least about 10% by weight water, calculated on the basis of the total weight of the composition. The cosmetic carrier particularly preferably contains water, in particular in such an amount that the cosmetic composition, calculated on the basis of its total weight, contains at least about 20% by weight, in particular at least about 40.0% by weight, most preferably about 70% by weight of water. Cosmetic compositions that are very particularly preferred comprise, in relation to their total weight, a water content between about 50 and about 95% by weight, preferably between about 60 and about 90% by weight, and in particular between about 65 and about 85% by weight.

As alcohols, the lower alcohols with from about 1 to about 4 carbon atoms usually used in particular for cosmetic purposes, such as ethanol and isopropanol, can be contained.

Examples of water-soluble solvents as cosolvents are glycerol and/or ethylene glycol and/or 1,2-propylene glycol in an amount of from about 0 to about 30% by weight in relation to the total product.

The composition of some preferred cosmetic agents can be deduced from the following tables (specified amounts in % by weight are in relation to the total weight of the cosmetic agent unless specified otherwise).

| | Formula 1 | Formula 2 | Formula 3 | Formula 4 | Formula 5 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| Misc | to 100 | to 100 | to 100 | to 100 | to 100 |

|  | Formula 1a | Formula 2a | Formula 3a | Formula 4a | Formula 5a |
| --- | --- | --- | --- | --- | --- |
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/ Dimethylaminoethyl Methacrylate Copolymer | 0.05 to 10 | 0.05 to 10 | 0.05 to 7.0 | 0.05 to 7.0 | 0.1 to 5.0 |
| Misc | to 100 | to 100 | to 100 | to 100 | to 100 |

|  | Formula 1b | Formula 2b | Formula 3b | Formula 4b | Formula 5b |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Advantage ® S (specified as solid content) | 0.05 to 10 | 0.05 to 10 | 0.05 to 7.0 | 0.05 to 7.0 | 0.1 to 5.0 |
| Misc | to 100 | to 100 | to 100 | to 100 | to 100 |

|  | Formula 1c | Formula 2c | Formula 3c | Formula 4c | Formula 5c |
| --- | --- | --- | --- | --- | --- |
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/ DMAPA Acrylates Copolymer | 0.05 to 10 | 0.05 to 10 | 0.05 to 7.0 | 0.05 to 7.0 | 0.1 to 5.0 |
| Misc | to 100 | to 100 | to 100 | to 100 | to 100 |

|  | Formula 1d | Formula 2d | Formula 3d | Formula 4d | Formula 5d |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| Misc | to 100 | to 100 | to 100 | to 100 | to 100 |

|  | Formula 6 | Formula 7 | Formula 8 | Formula 9 | Formula 10 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| Polyvinyl-pyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 6a | Formula 7a | Formula 8a | Formula 9a | Formula 10a |
| --- | --- | --- | --- | --- | --- |
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/ Dimethylaminoethyl Methacrylate Copolymer | 0.05 to 10 | 0.05 to 10 | 0.05 to 7.0 | 0.05 to 7.0 | 0.1 to 5.0 |
| Polyvinylpyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 6b | Formula 7b | Formula 8b | Formula 9b | Formula 10b |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Advantage ® S (specified as solid content) | 0.05 to 10 | 0.05 to 10 | 0.05 to 7.0 | 0.05 to 7.0 | 0.1 to 5.0 |
| Polyvinylpyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 6c | Formula 7c | Formula 8c | Formula 9c | Formula 10c |
| --- | --- | --- | --- | --- | --- |
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/DMAPA Acrylates Copolymer | 0.05 to 10 | 0.05 to 10 | 0.05 to 7.0 | 0.05 to 7.0 | 0.1 to 5.0 |
| Polyvinylpyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 6d | Formula 7d | Formula 8d | Formula 9d | Formula 10d |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| Polyvinylpyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 11 | Formula 12 | Formula 13 | Formula 14 | Formula 15 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| Vinyl-pyrrolidone/vinyl acetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 11a | Formula 12a | Formula 13a | Formula 14a | Formula 15a |
| --- | --- | --- | --- | --- | --- |
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/Dimethylaminoethyl Methacrylate Copolymer | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 11b | Formula 12b | Formula 13b | Formula 14b | Formula 15b |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Advantage ® S (specified as solid content) | 0.05 to 10 | 0.05 to 10 | 0.05 to 7.0 | 0.05 to 7.0 | 0.1 to 5.0 |

-continued

|  | Formula 11b | Formula 12b | Formula 13b | Formula 14b | Formula 15b |
|---|---|---|---|---|---|
| Vinylpyrrolidone/vinyl acetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 11c | Formula 12c | Formula 13c | Formula 14c | Formula 15c |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/ DMAPA Acrylates Copolymer | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 11d | Formula 12d | Formula 13d | Formula 14d | Formula 15d |
|---|---|---|---|---|---|
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 16 | Formula 17 | Formula 18 | Formula 19 | Formula 20 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| Carbomer | 0.02 to 3.0 | 0.05 to 2.0 | 0.05 to 1.5 | 0.2 to 1.5 | 0.2 to 0.8 |
| Misc | to 100 | to 100 | to 100 | to 100 | to 100 |

|  | Formula 16a | Formula 17a | Formula 18a | Formula 19a | Formula 20a |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/ Dimethylaminoethyl Methacrylate Copolymer | 0.05 to 10 | 0.05 to 10 | 0.05 to 7.0 | 0.05 to 7.0 | 0.1 to 5.0 |
| Carbomer | 0.02 to 3.0 | 0.05 to 2.0 | 0.05 to 1.5 | 0.2 to 1.5 | 0.2 to 0.8 |
| Misc | to 100 | to 100 | to 100 | to 100 | to 100 |

|  | Formula 16b | Formula 17b | Formula 18b | Formula 19b | Formula 20b |
|---|---|---|---|---|---|
| Luvigel ® Fit Up (specified as solid content) | 0.1 to 15 | 0.2 to 10 | 0.2 to 10 | 0.5 to 7.0 | 0.5 to 7.0 |
| Advantage ® S (specified as solid content) | 0.05 to 10 | 0.05 to 10 | 0.05 to 7.0 | 0.05 to 7.0 | 0.1 to 5.0 |

-continued

|  | Formula 16b | Formula 17b | Formula 18b | Formula 19b | Formula 20b |
|---|---|---|---|---|---|
| Carbomer | 0.02 to 3.0 | 0.05 to 2.0 | 0.05 to 1.5 | 0.2 to 1.5 | 0.2 to 0.8 |
| Misc | to 100 | to 100 | to 100 | to 100 | to 100 |

|  | Formula 16c | Formula 17c | Formula 18c | Formula 19c | Formula 20c |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/DMAPA Acrylates Copolymer | 0.05 to 10 | 0.05 to 10 | 0.05 to 7.0 | 0.05 to 7.0 | 0.1 to 5.0 |
| Carbomer | 0.02 to 3.0 | 0.05 to 2.0 | 0.05 to 1.5 | 0.2 to 1.5 | 0.2 to 0.8 |
| Misc | to 100 | to 100 | to 100 | to 100 | to 100 |

|  | Formula 16d | Formula 17d | Formula 18d | Formula 19d | Formula 20d |
|---|---|---|---|---|---|
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| Carbomer | 0.02 to 3.0 | 0.05 to 2.0 | 0.05 to 1.5 | 0.2 to 1.5 | 0.2 to 0.8 |
| Misc | to 100 | to 100 | to 100 | to 100 | to 100 |

|  | Formula 21 | Formula 22 | Formula 23 | Formula 24 | Formula 25 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| PEG-40 Hydrogenated Castor Oil | 0.05 to 1.5 | 0.1 to 1.0 | 0.2 to 0.8 | 0.3 to 0.8 | 0.3 to 0.6 |
| Misc | to 100 | to 100 | to 100 | to 100 | to 100 |

|  | Formula 21a | Formula 22a | Formula 23a | Formula 24a | Formula 25a |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/Dimethylaminoethyl Methacrylate Copolymer | 0.05 to 10 | 0.05 to 10 | 0.05 to 7.0 | 0.05 to 7.0 | 0.1 to 5.0 |
| PEG-40 Hydrogenated Castor Oil | 0.05 to 1.5 | 0.1 to 1.0 | 0.2 to 0.8 | 0.3 to 0.8 | 0.3 to 0.6 |
| Misc | to 100 | to 100 | to 100 | to 100 | to 100 |

|  | Formula 21b | Formula 22b | Formula 23b | Formula 24b | Formula 25b |
|---|---|---|---|---|---|
| Luvigel ® Fit Up (specified as solid content) | 0.1 to 15 | 0.2 to 10 | 0.2 to 10 | 0.5 to 7.0 | 0.5 to 7.0 |
| Advantage ® S (specified as solid content) | 0.05 to 10 | 0.05 to 10 | 0.05 to 7.0 | 0.05 to 7.0 | 0.1 to 5.0 |

|  | Formula 21b | Formula 22b | Formula 23b | Formula 24b | Formula 25b |
|---|---|---|---|---|---|
| PEG-40 Hydrogenated Castor Oil | 0.05 to 1.5 | 0.1 to 1.0 | 0.2 to 0.8 | 0.3 to 0.8 | 0.3 to 0.6 |
| Misc | to 100 | to 100 | to 100 | to 100 | to 100 |

|  | Formula 21c | Formula 22c | Formula 23c | Formula 24c | Formula 25c |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/DMAPA Acrylates Copolymer | 0.05 to 10 | 0.05 to 10 | 0.05 to 7.0 | 0.05 to 7.0 | 0.1 to 5.0 |
| PEG-40 Hydrogenated Castor Oil | 0.05 to 1.5 | 0.1 to 1.0 | 0.2 to 0.8 | 0.3 to 0.8 | 0.3 to 0.6 |
| Misc | to 100 | to 100 | to 100 | to 100 | to 100 |

|  | Formula 21d | Formula 22d | Formula 23d | Formula 24d | Formula 25d |
|---|---|---|---|---|---|
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| PEG-40 Hydrogenated Castor Oil | 0.05 to 1.5 | 0.1 to 1.0 | 0.2 to 0.8 | 0.3 to 0.8 | 0.3 to 0.6 |
| Misc | to 100 | to 100 | to 100 | to 100 | to 100 |

|  | Formula 26 | Formula 27 | Formula 28 | Formula 29 | Formula 30 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| Water | 50 to 95 | 50 to 95 | 60 to 90 | 60 to 90 | 65 to 85 |
| Misc | to 100 | to 100 | to 100 | to 100 | to 100 |

|  | Formula 26a | Formula 27a | Formula 28a | Formula 29a | Formula 30a |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/Dimethylaminoethyl Methacrylate Copolymer | 0.05 to 10 | 0.05 to 10 | 0.05 to 7.0 | 0.05 to 7.0 | 0.1 to 5.0 |
| Water | 50 to 95 | 50 to 95 | 60 to 90 | 60 to 90 | 65 to 85 |
| Misc | to 100 | to 100 | to 100 | to 100 | to 100 |

|  | Formula 26b | Formula 27b | Formula 28b | Formula 29b | Formula 30b |
|---|---|---|---|---|---|
| Luvigel ® Fit Up (specified as solid content) | 0.1 to 15 | 0.2 to 10 | 0.2 to 10 | 0.5 to 7.0 | 0.5 to 7.0 |
| Advantage ® S (specified as solid content) | 0.05 to 10 | 0.05 to 10 | 0.05 to 7.0 | 0.05 to 7.0 | 0.1 to 5.0 |

-continued

|  | Formula 26b | Formula 27b | Formula 28b | Formula 29b | Formula 30b |
|---|---|---|---|---|---|
| Water | 50 to 95 | 50 to 95 | 60 to 90 | 60 to 90 | 65 to 85 |
| Misc | to 100 | to 100 | to 100 | to 100 | to 100 |

|  | Formula 26c | Formula 27c | Formula 28c | Formula 29c | Formula 30c |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/DMAPA Acrylates Copolymer | 0.05 to 10 | 0.05 to 10 | 0.05 to 7.0 | 0.05 to 7.0 | 0.1 to 5.0 |
| Water | 50 to 95 | 50 to 95 | 60 to 90 | 60 to 90 | 65 to 85 |
| Misc | to 100 | to 100 | to 100 | to 100 | to 100 |

|  | Formula 26d | Formula 27d | Formula 28d | Formula 29d | Formula 30d |
|---|---|---|---|---|---|
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| Water | 50 to 95 | 50 to 95 | 60 to 90 | 60 to 90 | 65 to 85 |
| Misc | to 100 | to 100 | to 100 | to 100 | to 100 |

|  | Formula 31 | Formula 32 | Formula 33 | Formula 34 | Formula 35 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| Polyvinyl-pyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 31a | Formula 32a | Formula 33a | Formula 34a | Formula 35a |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/ Dimethylaminoethyl Methacrylate Copolymer | 0.05 to 10 | 0.05 to 10 | 0.05 to 7.0 | 0.05 to 7.0 | 0.1 to 5.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 31b | Formula 32b | Formula 33b | Formula 34b | Formula 35b |
|---|---|---|---|---|---|
| Luvigel ® Fit Up (specified as solid content) | 0.1 to 15 | 0.2 to 10 | 0.2 to 10 | 0.5 to 7.0 | 0.5 to 7.0 |
| Advantage ® S (specified as solid content) | 0.05 to 10 | 0.05 to 10 | 0.05 to 7.0 | 0.05 to 7.0 | 0.1 to 5.0 |

-continued

|  | Formula 31b | Formula 32b | Formula 33b | Formula 34b | Formula 35b |
|---|---|---|---|---|---|
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 31c | Formula 32c | Formula 33c | Formula 34c | Formula 35c |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/DMAPA Acrylates Copolymer | 0.05 to 10 | 0.05 to 10 | 0.05 to 7.0 | 0.05 to 7.0 | 0.1 to 5.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 31d | Formula 32d | Formula 33d | Formula 34d | Formula 35d |
|---|---|---|---|---|---|
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 36 | Formula 37 | Formula 38 | Formula 39 | Formula 40 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 36a | Formula 37a | Formula 38a | Formula 39a | Formula 40a |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/ Dimethylaminoethyl Methacrylate Copolymer | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 36b | Formula 37b | Formula 38b | Formula 39b | Formula 40b |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Advantage ® S (specified as solid content) | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 36c | Formula 37c | Formula 38c | Formula 39c | Formula 40c |
| --- | --- | --- | --- | --- | --- |
| Acrylates/$C_{10\text{-}30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/ DMAPA Acrylates Copolymer | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 36d | Formula 37d | Formula 38d | Formula 39d | Formula 40d |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 41 | Formula 42 | Formula 43 | Formula 44 | Formula 45 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| Carbomer | 0.02 to 3.0 | 0.05 to 2.0 | 0.05 to 1.5 | 0.2 to 1.5 | 0.2 to 0.8 |
| Water | 50 to 95 | 50 to 95 | 60 to 90 | 60 to 90 | 65 to 85 |
| Misc | to 100 | to 100 | to 100 | to 100 | to 100 |

|  | Formula 41a | Formula 42a | Formula 43a | Formula 44a | Formula 45a |
| --- | --- | --- | --- | --- | --- |
| Acrylates/$C_{10\text{-}30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/ Dimethylaminoethyl Methacrylate Copolymer | 0.05 to 10 | 0.05 to 10 | 0.05 to 7.0 | 0.05 to 7.0 | 0.1 to 5.0 |
| Carbomer | 0.02 to 3.0 | 0.05 to 2.0 | 0.05 to 1.5 | 0.2 to 1.5 | 0.2 to 0.8 |
| Water | 50 to 95 | 50 to 95 | 60 to 90 | 60 to 90 | 65 to 85 |
| Misc | to 100 | to 100 | to 100 | to 100 | to 100 |

|  | Formula 41b | Formula 42b | Formula 43b | Formula 44b | Formula 45b |
|---|---|---|---|---|---|
| Luvigel ® Fit Up (specified as solid content) | 0.1 to 15 | 0.2 to 10 | 0.2 to 10 | 0.5 to 7.0 | 0.5 to 7.0 |
| Advantage ® S (specified is solid content) | 0.05 to 10 | 0.05 to 10 | 0.05 to 7.0 | 0.05 to 7.0 | 0.1 to 5.0 |
| Carbomer | 0.02 to 3.0 | 0.05 to 2.0 | 0.05 to 1.5 | 0.2 to 1.5 | 0.2 to 0.8 |
| Water | 50 to 95 | 50 to 95 | 60 to 90 | 60 to 90 | 65 to 85 |
| Misc | to 100 | to 100 | to 100 | to 100 | to 100 |

|  | Formula 41c | Formula 42c | Formula 43c | Formula 44c | Formula 45c |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/ DMAPA Acrylates Copolymer | 0.05 to 10 | 0.05 to 10 | 0.05 to 7.0 | 0.05 to 7.0 | 0.1 to 5.0 |
| Carbomer | 0.02 to 3.0 | 0.05 to 2.0 | 0.05 to 1.5 | 0.2 to 1.5 | 0.2 to 0.8 |
| Water | 50 to 95 | 50 to 95 | 60 to 90 | 60 to 90 | 65 to 85 |
| Misc | to 100 | to 100 | to 100 | to 100 | to 100 |

|  | Formula 41d | Formula 42d | Formula 43d | Formula 44d | Formula 45d |
|---|---|---|---|---|---|
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| Carbomer | 0.02 to 3.0 | 0.05 to 2.0 | 0.05 to 1.5 | 0.2 to 1.5 | 0.2 to 0.8 |
| Water | 50 to 95 | 50 to 95 | 60 to 90 | 60 to 90 | 65 to 85 |
| Misc | to 100 | to 100 | to 100 | to 100 | to 100 |

|  | Formula 46 | Formula 47 | Formula 48 | Formula 49 | Formula 50 |
|---|---|---|---|---|---|
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 46a | Formula 47a | Formula 48a | Formula 49a | Formula 50a |
|---|---|---|---|---|---|
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/ Dimethylaminoethyl Methacrylate Copolymer | 0.05 to 10 | 0.05 to 10 | 0.05 to 7.0 | 0.05 to 7.0 | 0.1 to 5.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 46b | Formula 47b | Formula 48b | Formula 49b | Formula 50b |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Advantage ® S (specified as solid content) | 0.05 to 10 | 0.05 to 10 | 0.05 to 7.0 | 0.05 to 7.0 | 0.1 to 5.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 46c | Formula 47c | Formula 48c | Formula 49c | Formula 50c |
| --- | --- | --- | --- | --- | --- |
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/ DMAPA Acrylates Copolymer | 0.05 to 10 | 0.05 to 10 | 0.05 to 7.0 | 0.05 to 7.0 | 0.1 to 5.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 46d | Formula 47d | Formula 48d | Formula 49d | Formula 50d |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 51 | Formula 52 | Formula 53 | Formula 54 | Formula 55 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| Polyvinylpyrrolidone | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 51a | Formula 52a | Formula 53a | Formula 54a | Formula 55a |
| --- | --- | --- | --- | --- | --- |
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/ Dimethylaminoethyl Methacrylate Copolymer | 0.05 to 10 | 0.05 to 10 | 0.05 to 7.0 | 0.05 to 7.0 | 0.1 to 5.0 |

|  | Formula 51a | Formula 52a | Formula 53a | Formula 54a | Formula 55a |
| --- | --- | --- | --- | --- | --- |
| Polyvinylpyrrolidone | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 51b | Formula 52b | Formula 53b | Formula 54b | Formula 55b |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Advantage ® S (specified as solid content) | 0.05 to 10 | 0.05 to 10 | 0.05 to 7.0 | 0.05 to 7.0 | 0.1 to 5.0 |
| Polyvinylpyrrolidone | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 51c | Formula 52c | Formula 53c | Formula 54c | Formula 55c |
| --- | --- | --- | --- | --- | --- |
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/ DMAPA Acrylates Copolymer | 0.05 to 10 | 0.05 to 10 | 0.05 to 7.0 | 0.05 to 7.0 | 0.1 to 5.0 |
| Polyvinylpyrrolidone | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 51d | Formula 52d | Formula 53d | Formula 54d | Formula 55d |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| Polyvinylpyrrolidone | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 56 | Formula 57 | Formula 58 | Formula 59 | Formula 60 |
| --- | --- | --- | --- | --- | --- |
| Copolymer a) | 0.1 to 15 | 0.2 to 10 | 0.2 to 10 | 0.5 to 7.0 | 0.5 to 7.0 |
| Copolymer b) | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |

|  | Formula 56 | Formula 57 | Formula 58 | Formula 59 | Formula 60 |
| --- | --- | --- | --- | --- | --- |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 56a | Formula 57a | Formula 58a | Formula 59a | Formula 60a |
| --- | --- | --- | --- | --- | --- |
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| Vinyl Caprolactam/VP/ Dimethylaminoethyl Methacrylate Copolymer | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 56b | Formula 57b | Formula 58b | Formula 59b | Formula 60b |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Advantage ® S (specified as solid content) | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 56c | Formula 57c | Formula 58c | Formula 59c | Formula 60c |
| --- | --- | --- | --- | --- | --- |
| Acrylates/$C_{10-30}$-Alkyl Methacrylate Copolymer | 0.1 to 15 | 0.2 to 10 | 0.2 to 10 | 0.5 to 7.0 | 0.5 to 7.0 |
| VP/Vinyl Caprolactam/ DMAPA Acrylates Copolymer | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 56d | Formula 57d | Formula 58d | Formula 59d | Formula 60d |
| --- | --- | --- | --- | --- | --- |
| Luvigel ® Fit Up (specified as solid content) | 0.1 to 15 | 0.2 to 10 | 0.2 to 10 | 0.5 to 7.0 | 0.5 to 7.0 |
| Aquaflex ® SF 40 (specified as solid content) | 0.05 to 10 | 0.05 to 10 | 0.05 to 7.0 | 0.05 to 7.0 | 0.1 to 5.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| PEG-40 Hydrogenated Castor Oil | 0.05 to 1.5 | 0.1 to 1.0 | 0.2 to 0.8 | 0.3 to 0.8 | 0.3 to 0.6 |

-continued

|  | Formula 56d | Formula 57d | Formula 58d | Formula 59d | Formula 60d |
|---|---|---|---|---|---|
| Water | 50 to 95 | 50 to 95 | 60 to 90 | 60 to 90 | 65 to 85 |
| Misc | to 100 | to 100 | to 100 | to 100 | to 100 |

The entry "Misc" is to be understood as contemplated herein to mean a cosmetic carrier, in particular water (unless listed separately) and optionally further usual constituents of styling products.

The cosmetic composition of the present disclosure can be provided in the forms that are usual for the temporary reshaping of hair, for example as a hair gel, hairspray, hair mousse, or hair wax. The cosmetic composition is preferably provided as a hair gel.

Both hair mousses and hairsprays require the presence of propellants. As contemplated herein, however, no hydrocarbons or only small quantities of hydrocarbons should preferably be used for this. Propane, propane/butane mixtures and dimethyl ethers are particularly suitable propellants as contemplated herein.

The present disclosure also relates to the use of cosmetic compositions as contemplated herein for temporarily reshaping keratin fibres, in particular human hair, and to a method for the temporary deformation of keratin fibres, in particular human hair, in which the cosmetic composition as contemplated herein is applied to keratin fibres and the form of said fibres is temporarily fixed.

A further subject of this patent application is the use of a cosmetic composition as contemplated herein to improve the hold of temporarily deformed keratin fibres.

A last subject matter of this patent application is the use of a cosmetic composition as contemplated herein to improve the moisture resistance of temporarily deformed keratin fibres.

EXAMPLES

The following hair gels were prepared:

| Component/raw material | INCI name or chemical name | V1 | V2 | E1 |
|---|---|---|---|---|
| Luvigel ® Fit UP [1] | Acrylates (C10-30) Alkyl Methacrylate Copolymer | 3.33 | — | 1.66 |
| Advantage ® S [2] | Vinyl Caprolactam/VP/Dimethylamino-ethyl Methacrylate Copolymer | — | 1.0 | 0.5 |
| AMP-ULTRA PC 2000 | Aminomethyl Propanol | 0.45 | — | 0.23 |
| Water |  | 96.22 | 99.0 | 97.61 |
| Total |  | 100 | 100 | 100 |

[1] 30 by weight active substance in water
[2] 100 by weight active substance in water The amounts specified in the table are given in % by weight of the respective raw materials, in relation to the total composition. The polymer content in each of the compositions V1, V2 and E1 was 1.0% by weight.

The moisture resistance of cleaned strands of Kerling hair was determined for the obtained styling agents by employing an HHCR test (high humidity curl retention test: 6 h; mean value from 5 hair strands in each case):

|  | V1 | V2 | E1 |
|---|---|---|---|
| HHCR | 62% | 54% | 81% |

The polymer combination E1 as contemplated herein therefore demonstrated a synergistic effect, going considerably beyond a purely additive effect, in respect of the moisture resistance.

II. The following further hair gels were prepared:

| Component/raw material | INCI name or chemical name | V1 | V2 | E1 |
|---|---|---|---|---|
| Luvigel ® Fit UP [1] | Acrylates (C10-30) Alkyl Methacrylate Copolymer | 3.33 | — | 1.66 |

-continued

| Component/raw material | INCI name or chemical name | V1 | V2 | E1 |
|---|---|---|---|---|
| Aquaflex ® SF 40 [2] | VP/Vinyl Caprolactam/DMAPA Acrylates Copolymer | — | 2.50 | 1.25 |
| AMP-ULTRA PC 2000 | Aminomethyl Propanol | 0.45 | — | 0.23 |
| Water |  | 96.22 | 97.50 | 96.86 |
| Total |  | 100 | 100 | 100 |

[1] 30% by weight active substance in water
[2] 40% by weight active substance in water The amounts specified in the table are given in % by weight of the respective raw materials, in relation to the total composition. The polymer content in each of the compositions V1, V2 and E1 was 1.0% by weight.

The moisture resistance of cleaned strands of Kerling hair was determined for the obtained styling agents by employing an HHCR test (high humidity curl retention test: 6 h; mean value from 5 hair strands in each case):

|  | V1 | V2 | E1 |
|---|---|---|---|
| HHCR | 62% | 39% | 71% |

The polymer combination E1 as contemplated herein therefore demonstrated a synergistic effect, going considerably beyond a purely additive effect, in respect of the moisture resistance.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for temporarily reshaping keratin fibres, said composition comprising:
   a) at least one non-cross-linked, hydrophobically modified (meth)acrylic acid copolymer a), wherein the at least one copolymer a) comprises a compound with the International Nomenclature Cosmetic Ingredient (INCI) name Acrylates/$C_{10-30}$ Alkyl Methacrylate Copolymer; and
   b) at least one vinyl caprolactam copolymer b), wherein the at least one copolymer b) comprises a copolymer of vinyl caprolactam, vinyl pyrrolidone, and dimethylaminoethyl methacrylate, having the INCI name Vinyl Caprolactam/VP/Dimethylaminoethyl Methacrylate Copolymer;
   wherein the proportion by weight of the copolymer a) in the total weight of the composition is about 0.5% by weight, and the proportion by weight of the copolymer b) in the total weight of the composition is about 0.5% by weight.

2. The cosmetic composition according to claim 1, wherein the copolymer a) consists of the compound with the INCI name Acrylates/$C_{10-30}$ Alkyl Methacrylate Copolymer, and wherein the copolymer b) consists of the compound with the INCI name Vinyl Caprolactam/VP/Dimethylaminoethyl Methacrylate Copolymer.

3. The cosmetic composition according to claim 1, wherein the cosmetic composition consists of:
   the compound with the INCI name Acrylates/$C_{10-30}$ Alkyl Methacrylate Copolymer at about 0.5 weight percent, based on a total weight of the cosmetic composition;
   the compound having the INCI name Vinyl Caprolactam/VP/Dimethylaminoethyl Methacrylate Copolymer at about 0.5 weight percent, based on the total weight of the cosmetic composition;
   aminomethyl propanol; and
   water.

4. The cosmetic composition according to claim 3, wherein the aminomethyl propanol is at about 0.2 weight percent and the water is at about 97.6 weight percent, based on the total weight of the cosmetic composition.

5. A cosmetic composition for the temporary shaping of keratinic fibers, comprising polymers and other components, and wherein the polymers consist of a compound with the International Nomenclature Cosmetic Ingredient (INCI) name Acrylates/$C_{10-30}$ Alkyl Methacrylate Copolymer in an amount of about 0.5 weight percent, based on a total weight of the cosmetic composition, and a copolymer of vinyl caprolactam, vinyl pyrrolidone, and dimethylaminoethyl methacrylate, having the INCI name Vinyl Caprolactam/VP/Dimethylaminoethyl Methacrylate Copolymer in an amount of about 0.5 weigh percent, based on the total weight of the cosmetic composition; and
   wherein the cosmetic composition further comprises water in an amount of at least about 70%, based on the total weight of the cosmetic composition.

6. The cosmetic composition according to claim 5, wherein the cosmetic composition further comprises:
   the water at about 97.6 weight percent, based on the total weight of the cosmetic composition; and
   aminomethyl propanol at about 0.2 weight percent, based on the total weight of the cosmetic composition.

7. The cosmetic composition according to claim 5, wherein the composition further comprises aminomethyl propanol.

8. The cosmetic composition according to claim 7, wherein the composition comprises the aminomethyl propanol in an amount of about 0.2 weight percent, based on the total weight of the cosmetic composition.

9. A method for the temporary deformation of keratinous fibres, in which the keratin fibres are exposed to a cosmetic composition according to claim 1 and are fixed temporarily in their form.

* * * * *